(12) United States Patent
Chouinard

(10) Patent No.: US 9,839,764 B2
(45) Date of Patent: *Dec. 12, 2017

(54) CATHETER INCLUDING A BARE METAL HYPOTUBE

(71) Applicant: Boston Scientific Scientific Scimed, Inc., Maple Grove, MN (US)

(72) Inventor: Paul F. Chouinard, Maple Grove, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 383 days.

This patent is subject to a terminal disclaimer.

(21) Appl. No.: 14/556,461

(22) Filed: Dec. 1, 2014

(65) Prior Publication Data

US 2015/0088065 A1    Mar. 26, 2015

Related U.S. Application Data

(63) Continuation of application No. 13/666,648, filed on Nov. 1, 2012, now Pat. No. 8,911,398.
(Continued)

(51) Int. Cl.
*A61M 25/00* (2006.01)
*A61F 2/958* (2013.01)
(Continued)

(52) U.S. Cl.
CPC ......... *A61M 25/0052* (2013.01); *A61F 2/958* (2013.01); *A61M 25/0013* (2013.01);
(Continued)

(58) Field of Classification Search
CPC .............. A61M 25/0052; A61M 25/10; A61M 25/0013; A61M 25/0029; A61M 25/0054;
(Continued)

(56) References Cited

U.S. PATENT DOCUMENTS 5,106,455 A    4/1992  Jacobsen et al.
5,156,594 A *  10/1992  Keith ................ A61M 25/0662
                                                    604/103.09
(Continued)

FOREIGN PATENT DOCUMENTS

EP    2093311 A2    8/2009
WO    2010111446 A2    9/2010

OTHER PUBLICATIONS

Sedlacek et al. (Surface Topography Modelling for Reduced Friction. Strojniski vestnik—Journal of Mechanical Engineering 57(2011)9, p. 674-680).*

*Primary Examiner* — Imani Hayman
*Assistant Examiner* — Hamza Darb
(74) *Attorney, Agent, or Firm* — Seager, Tufte & Wickhem LLP.

(57) ABSTRACT

Catheter and methods for designing, making, and using catheters are disclosed. An example catheter is a balloon catheter. The balloon catheter may include a proximal shaft. The proximal shaft may be a bare metal hypotube having a skew value of −1.0 to −2.5. A midshaft may be attached to the proximal shaft. A distal shaft may be attached to the midshaft. A balloon may be coupled to the distal shaft. An inflation lumen may be defined that extends from the proximal shaft, through the midshaft, and into the distal shaft. The inflation lumen may be in fluid communication with the balloon.

19 Claims, 14 Drawing Sheets

Related U.S. Application Data

(60) Provisional application No. 61/555,993, filed on Nov. 4, 2011.

(51) Int. Cl.
*A61M 25/10* (2013.01)
*A61M 25/01* (2006.01)

(52) U.S. Cl.
CPC .... *A61M 25/0029* (2013.01); *A61M 25/0054* (2013.01); *A61M 25/10* (2013.01); *A61M 25/0032* (2013.01); *A61M 2025/0046* (2013.01); *A61M 2025/0063* (2013.01); *A61M 2025/0183* (2013.01)

(58) Field of Classification Search
CPC ...... A61M 25/0032; A61M 2025/0063; A61M 2025/0183; A61M 2025/0046
See application file for complete search history.

(56) References Cited

U.S. PATENT DOCUMENTS

| | | |
|---|---|---|
| 5,720,724 A | 2/1998 | Ressemann et al. |
| 5,772,609 A | 6/1998 | Nguyen et al. |
| 5,833,632 A | 11/1998 | Jacobsen et al. |
| 6,139,570 A | 10/2000 | Saadat et al. |
| 6,361,529 B1 | 3/2002 | Goodin |
| 6,409,863 B1 | 6/2002 | Williams et al. |
| 6,475,187 B1 | 11/2002 | Gerberding et al. |
| 6,579,246 B2 | 6/2003 | Jacobsen et al. |
| 6,766,720 B1 | 7/2004 | Jacobsen et al. |
| 8,057,430 B2 | 11/2011 | Grovender et al. |
| 2002/0165536 A1 | 11/2002 | Kelley et al. |
| 2003/0069522 A1 | 4/2003 | Jacobsen et al. |
| 2004/0181174 A2 | 9/2004 | Davis et al. |
| 2006/0264914 A1 | 11/2006 | Furst et al. |
| 2007/0135763 A1* | 6/2007 | Musbach .......... A61M 25/0054 604/96.01 |
| 2010/0217234 A1 | 8/2010 | Grovender et al. |
| 2011/0009942 A1 | 1/2011 | Gregorich et al. |

\* cited by examiner

CATHETER INCLUDING A BARE METAL HYPOTUBE

CROSS-REFERENCE TO RELATED APPLICATIONS

This application is a continuation of U.S. patent application Ser. No. 13/666,648 filed on Nov. 1, 2012, which claims benefit to U.S. Provisional Patent Application No. 61/555,993, filed Nov. 4, 2011, the entirety of which is incorporated herein by reference.

TECHNICAL FIELD

The present invention relates generally to catheters for performing medical procedures. More particularly, the present invention relates to catheters including a bare metal hypotube.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

The invention provides design, material, manufacturing method, and use alternatives for medical devices. An example medical device may include a balloon catheter. The balloon catheter may include a proximal shaft. The proximal shaft may be a bare metal hypotube having a skew value of −1.0 to −2.5. A midshaft may be attached to the proximal shaft. A distal shaft may be attached to the midshaft. A balloon may be coupled to the distal shaft. An inflation lumen may be defined that extends from the proximal shaft, through the midshaft, and into the distal shaft. The inflation lumen may be in fluid communication with the balloon.

Another example medical device may include a catheter. The catheter may include a catheter shaft. At least a portion of the catheter shaft may include a bare metal hypotube that is free of an outer lubricious coating. The bare metal hypotube may have a skew value of −1.0 to −2.5.

A method for designing a medical device is also disclosed. The method may include providing a bare metal hypotube and determining the skew value of the bare metal hypotube. If the skew value of the bare metal hypotube is −1.0 to −2.5, the method may also include manufacturing a catheter shaft that includes the bare metal hypotube.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
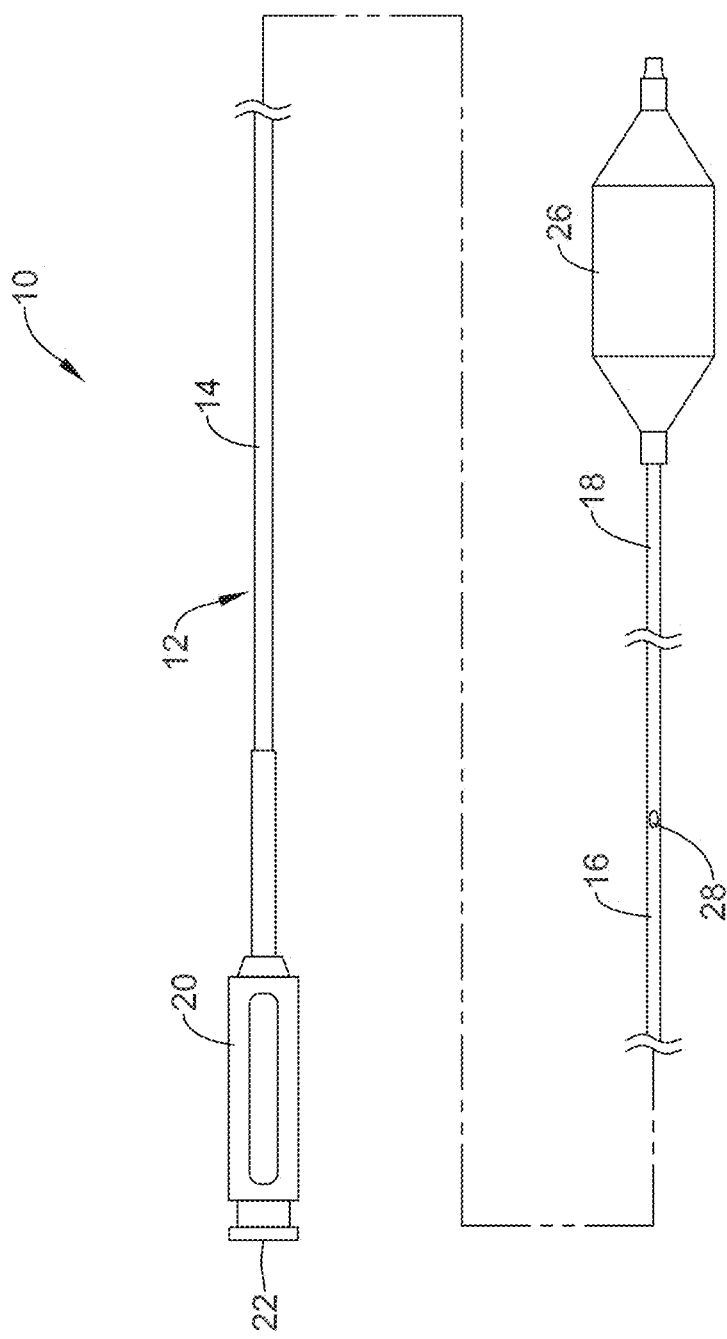
FIG. 1 is a plan view of an example balloon catheter.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

FIG. 1 is a plan view of an example catheter 10, for example a balloon catheter. Catheter 10 may include a catheter shaft 12 having a proximal shaft portion 14, a midshaft portion 16 and a distal shaft portion 18. In some embodiments, proximal shaft portion 14 may be a metallic hypotube. Midshaft portion 16 may be fitted over, fitted within, or abut proximal shaft portion 14, as appropriate. Likewise, distal shaft portion 18 may be fitted over, fitted within, or abut midshaft portion 16. These are just examples as any suitable arrangement may be utilized. A hub 20 may be attached to proximal shaft portion 14. Hub 20 may include one or more ports such as, for example, a port 22.

Figure 2:
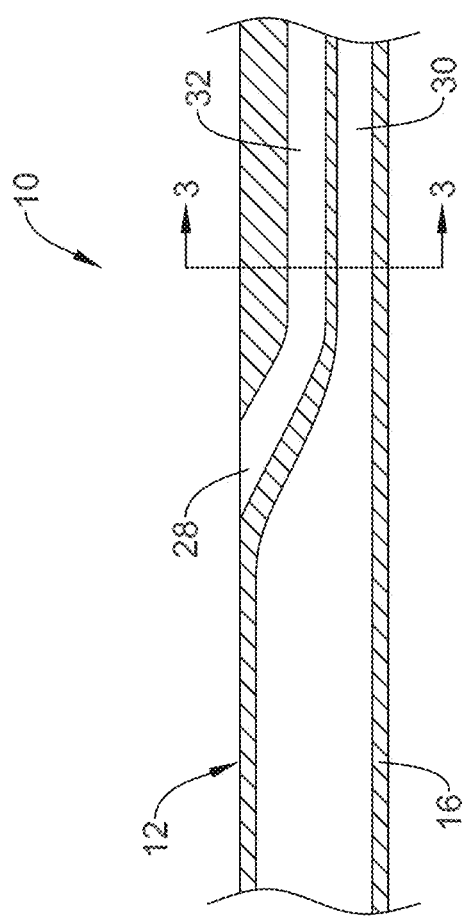
FIG. 2 is a cross-sectional view of a portion of the example balloon catheter shown in FIG. 1.
Figure 3:
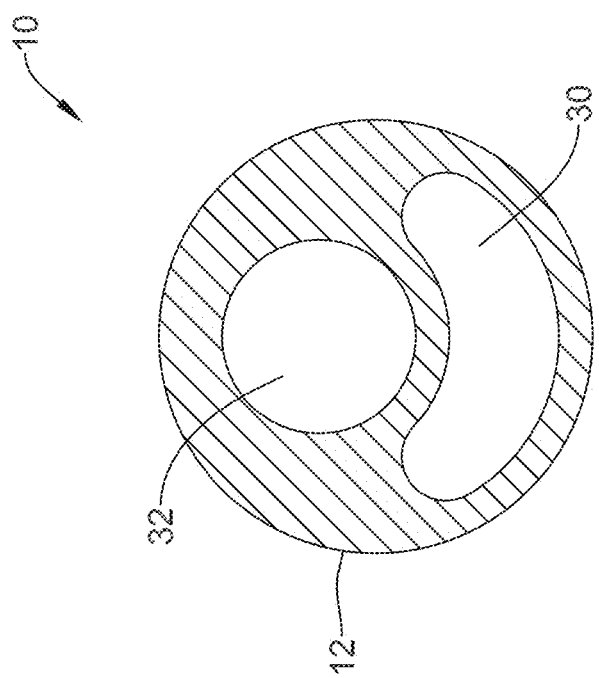
FIG. 3 is a cross-sectional view taken through line 3-3 in FIG. 2.

An expandable balloon 26 may be attached to distal shaft portion 18. Balloon 26 may be expanded by infusing inflation media through an inflation lumen 30, which is shown in FIG. 2. In at least some embodiments, port 22 may provide access to inflation lumen 30. Accordingly, a suitable inflation device may be attached to port 22 and inflation media may be passed through inflation lumen 30 to inflate balloon 26. Along a region of midshaft portion 16, inflation lumen 30 may have an annular shape as seen in FIG. 3. This may be due to the formation of a guidewire port 28 in midshaft portion 16. Some additional details regarding the formation of guidewire port 28 and/or inflation lumen 30 are provided herein.

As indicated above, guidewire port 28 may be formed in midshaft portion 16. For example, guidewire port 28 may be an opening extending through the wall of midshaft portion 16 that provides access to a guidewire lumen 32. In the embodiment depicted in FIG. 2, guidewire port 28 is positioned at a location that is distal to the proximal end of catheter shaft 12. When so arranged, catheter 10 may be a single-operator-exchange or rapid-exchange catheter, which allows catheter 10 to be used with a shorter guidewire. As such, guidewire lumen 32 may extend over only a portion of the length of catheter shaft 12. For example, guidewire lumen 32 may extend along distal shaft portion 18 and part of midshaft portion 16. Other embodiments, however, are contemplated where catheter 10 is an over-the-wire catheter or fixed wire catheter. In these embodiments, guidewire lumen 32 may extend along essentially the entire length of catheter shaft 12.

Catheter 10 may also include other structures that may be commonly associated with catheters. For example, a core wire (not shown) may be disposed within a portion of inflation lumen 30. The core wire may extend across midshaft portion 16 and may further improve the transition in flexibility along the length of catheter shaft 12 and/or improve catheter pushability. In addition, catheter 10 may include one or more radiopaque markers or bands, which may aid in fluoroscopically imaging catheter 10. These are just examples.

Figure 4:
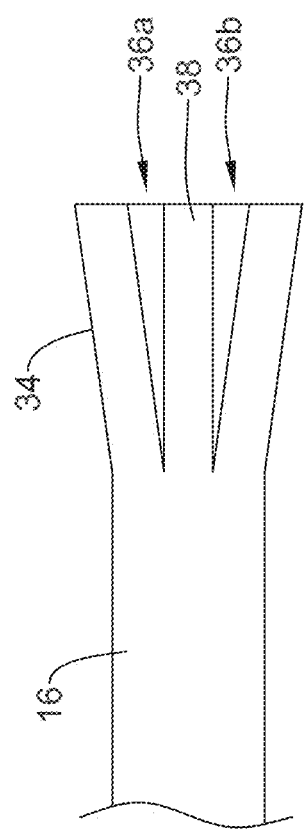
FIGS. 4-9 illustrate some of the example method steps for manufacturing the balloon catheter shown in FIG. 1-3.

FIGS. 4-9 illustrate some of the processing steps that may be utilized to form catheter 10 and/or catheter shaft 12. For example, FIG. 4 shows part of midshaft portion 16. Here it can be seen that a distal end 34 of midshaft portion 16 may be flared or otherwise enlarged. In addition, one or more cuts or slots, for example cuts 36a/36b, may be formed in distal end 34 of midshaft portion 16. A tongue 38 may be defined between cuts 36a/36b.

Figure 5:
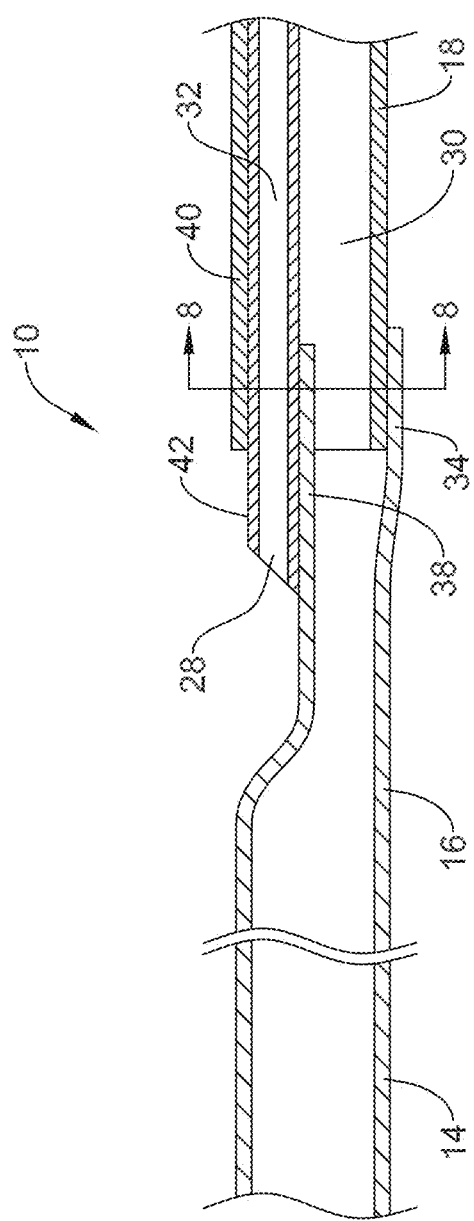
Figure 6:
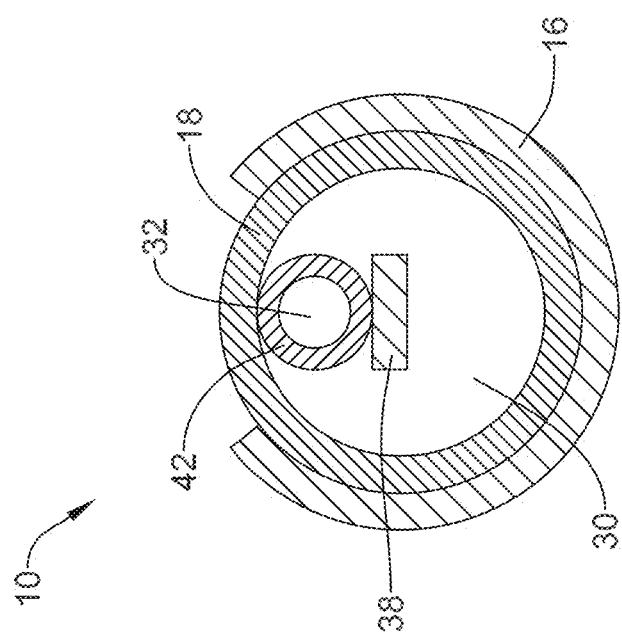

A proximal end 40 of distal shaft portion 18 may be disposed within the enlarged distal end 34 of midshaft portion 16 as shown in FIG. 5. In doing so, tongue 38 may be pressed inward and form a shelf or ledge. A distal inner tube 42 may be disposed within distal shaft portion 18 and may rest upon the ledge formed by tongue 38. Distal inner tube 42 may ultimately form guidewire lumen 32 as described in more detail below. The arrangement of distal inner tube 42 relative to tongue 38, midshaft portion 16, and distal shaft portion 18 can also be seen in FIG. 6.

Figure 7:
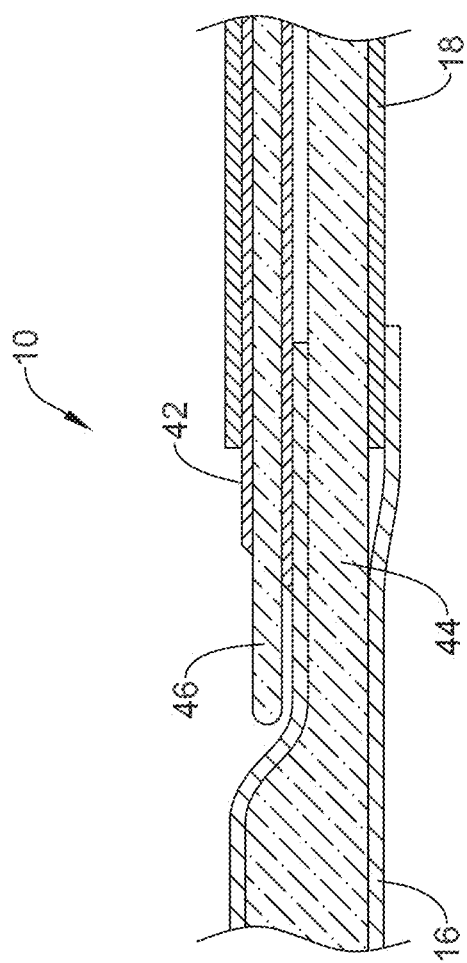
Figure 8:
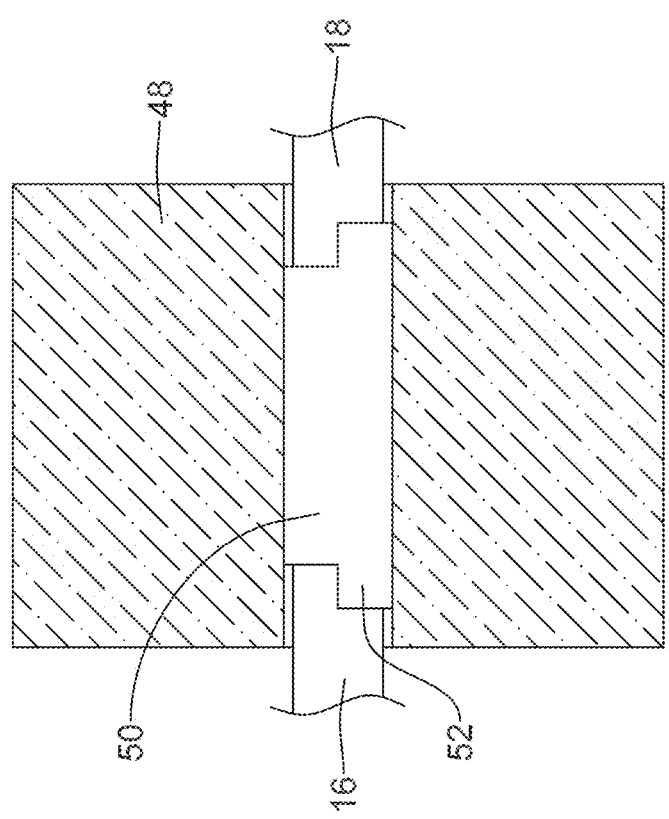
Figure 9:
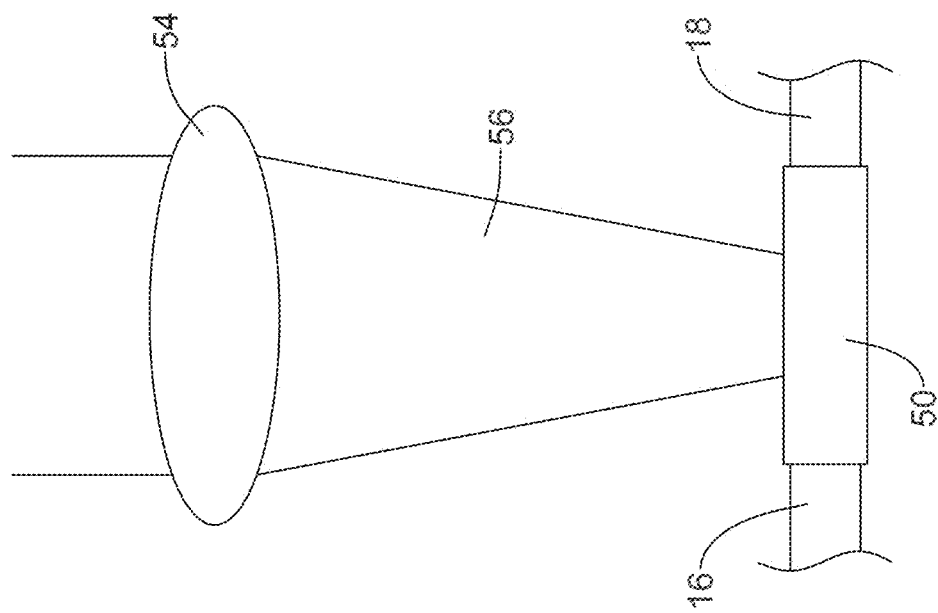

When suitably arranged, a first mandrel 44 may be inserted within a portion of distal shaft portion 18 and midshaft portion 16 as shown in FIG. 7. Likewise, a second mandrel 46 may be inserted within distal inner tube 42. With mandrels 44/46 in place, midshaft portion 16 and distal shaft portion 18 may be disposed within a compression fixture 48 as shown in FIG. 8. A sleeve 50 may be disposed over a region of midshaft portion 16 and distal shaft portion 18. Sleeve 50 may include one or more flanking ears 52, which may aid in removal of sleeve 50 upon completion of the manufacturing process. Finally, heat may be applied to sleeve 50. This may include the use of a lens 54 to focus heat (e.g., laser energy 56) onto sleeve 50 as depicted in FIG. 9. When heated, midshaft portion 16, distal shaft portion 18, and distal inner tube 42 may melt together. Mandrels 44/46 can be removed, thereby defining inflation lumen 30 and guidewire lumen 32, respectively, and the result may be the formation of catheter shaft 12 as shown in FIGS. 1-3.

Historically, the construction of balloon catheters has included the coating of the catheter shaft and/or the proximal portion of the catheter shaft with a lubricious material. For example, the proximal shaft portion in balloon catheters is typically coated and/or covered with a nylon material and/or a polytetrafluoroethylene (PTFE) coating to increase the lubricity of the catheter shaft. Such coatings may allow for the catheter to more easily navigate the anatomy and/or more easily be pushed through a guide catheter. While coating the proximal shaft portion does provide the catheter with a number of desirable features, coating the proximal shaft portion adds to the profile and manufacturing costs of the device.

In at least some embodiments, proximal shaft portion 14 is purposefully designed to be a "bare metal" tubular member that is free of an exterior coating (e.g., free of an outer lubricious coating). For example, proximal shaft portion 14 may be a stainless steel hypotube that is free of an outer lubricous coating. Other materials (including those metallic materials disclosed herein) free of an outer lubricious coating may also be used for proximal shaft portion 14. The use of bare metal tubular members may be desirable for a number of reasons including, for example, allowing catheter 10 (e.g., along proximal shaft portion 14) to have a smaller profile and a reduction manufacturing costs.

In addition, the bare metal proximal shaft portion 14 may also be selected to have a skew value falling within a particular range. For the purposes of this disclosure, skew ($R_{sk}$) is a measure of asymmetry of the profile about the mean line calculated over the evaluation length. Skew may also be understood to be the same as skewness or $R_{sk}$. Accordingly, a negative value of $R_{sk}$ indicates that the surface is made up of valleys, whereas a surface with a positive skew is said to contain mainly peaks. A negatively skewed surface is generally thought to be a lower friction surface. Thus, by careful selection of tubular members having the desired value of skew, catheter 10 can be manufactured to have the desired level of lubricity (e.g., the desired lower friction properties) while also allowing the profile of catheter 10 and manufacturing costs to both be reduced.

In at least some embodiments, catheter 10 includes a bare metal (e.g., free of an outer lubricious coating) proximal shaft portion 14 with a skew value that is about −1.0 or less, within the range of about −1.0 to −2.5, within the range of about −1.0 to −2.0, within the range of about −1.0 to −1.75, within the range of about −1.25 to −1.8, within the range of about −1.4 to −1.8, within the range of about −1.42 to −1.79, within the range of about −1.47 to −1.75, or within the range of about −1.57 to −1.74. These are just examples.

One example hypotube that may be used to form proximal shaft portion 14 in catheter 10 (and/or other catheters disclosed herein) is a bare metal (e.g., free of an outer lubricious coating) stainless steel hypotube commercially available from Cambus Medical (Galway, Ireland). Such tubular members may have a skew value falling within the range disclosed herein. Not only can these tubular members be utilized in catheter 10 (and/or other catheters and catheter shafts disclosed herein), these tubular members may be used in other medical devices including, for example, guidewires, guide catheters, other catheters (e.g., balloon catheters, etc.), stent or endoprosthesis delivery catheters, etc.

The design and/or manufacturing process for designing catheter 10 may include providing a tubular member and determining the skew value for the tubular member. If the skew values falls within the range disclosed herein, the tubular member may be used to manufacture, for example, proximal shaft portion 14 in catheter 10. It can be appreciated that if the skew value does fall within the range disclosed herein, not only can the tubular members be proximal shaft portion 14 in catheter 10, these tubular members may be used in other medical devices including, for example, guidewires, guide catheters, other catheters (e.g., balloon catheters, etc.), stent or endoprosthesis delivery catheters, etc. In these embodiments, the tubular member may be utilized as a bare metal tubular member and the finished medical device (e.g., catheter 10) is free of a coating on the bare metal tubular member.

Figure 10:
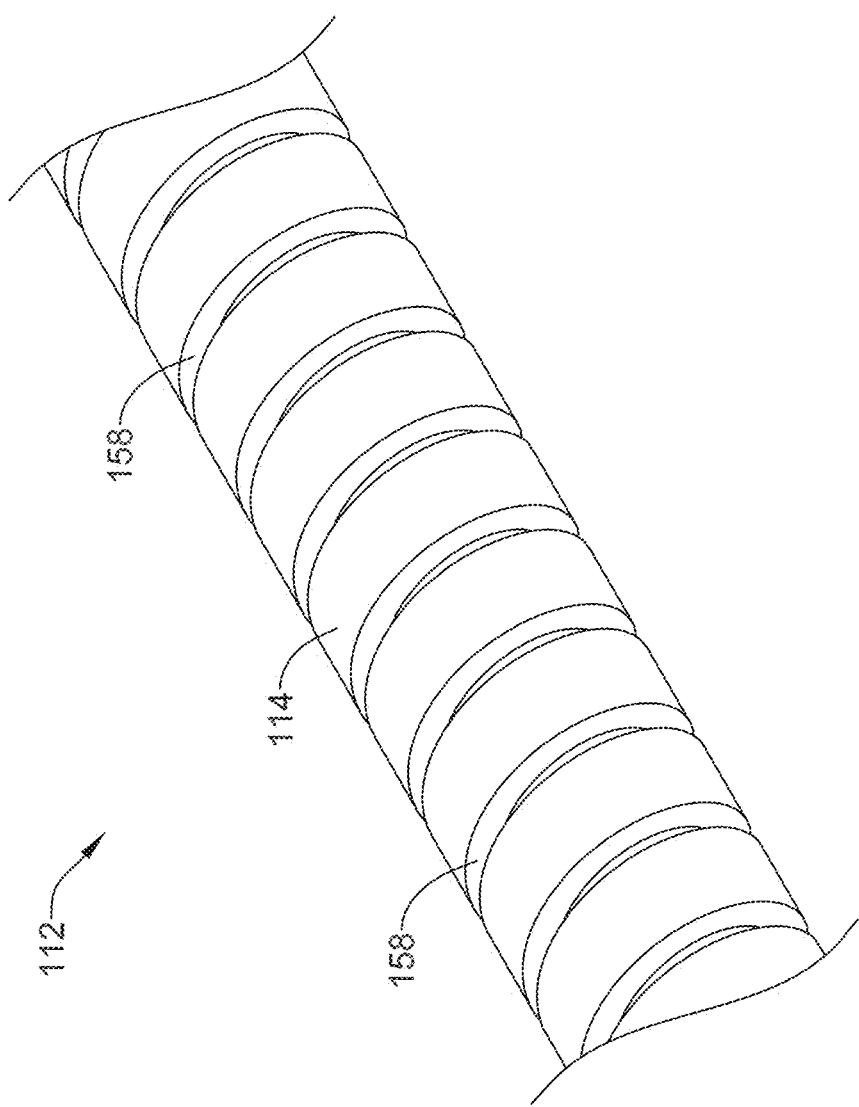
FIG. 10 is a perspective view of an example proximal shaft portion of a catheter shaft.
Figure 11:
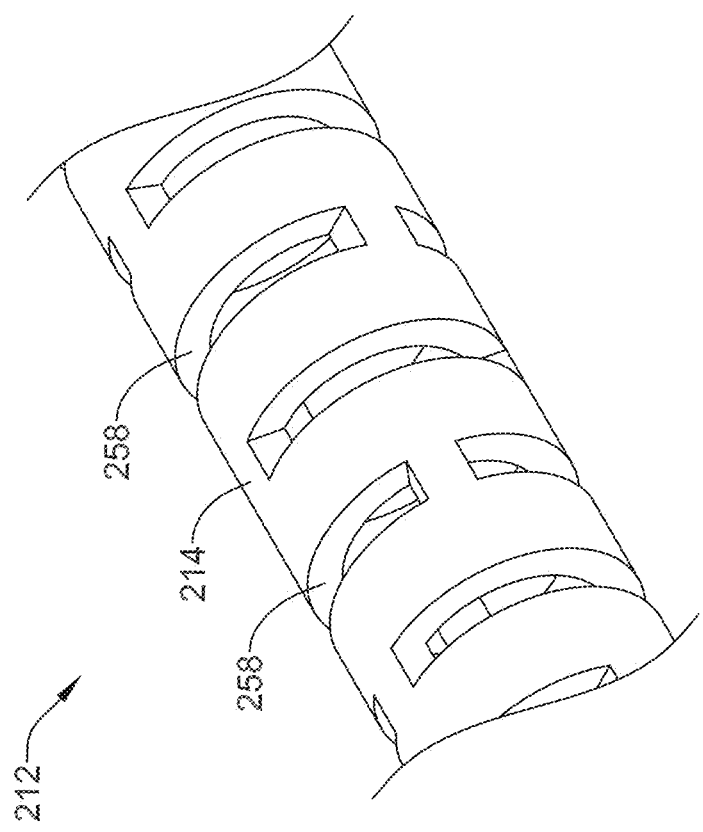
FIG. 11 is a perspective view of another example proximal shaft portion of a catheter shaft.
Figure 12:
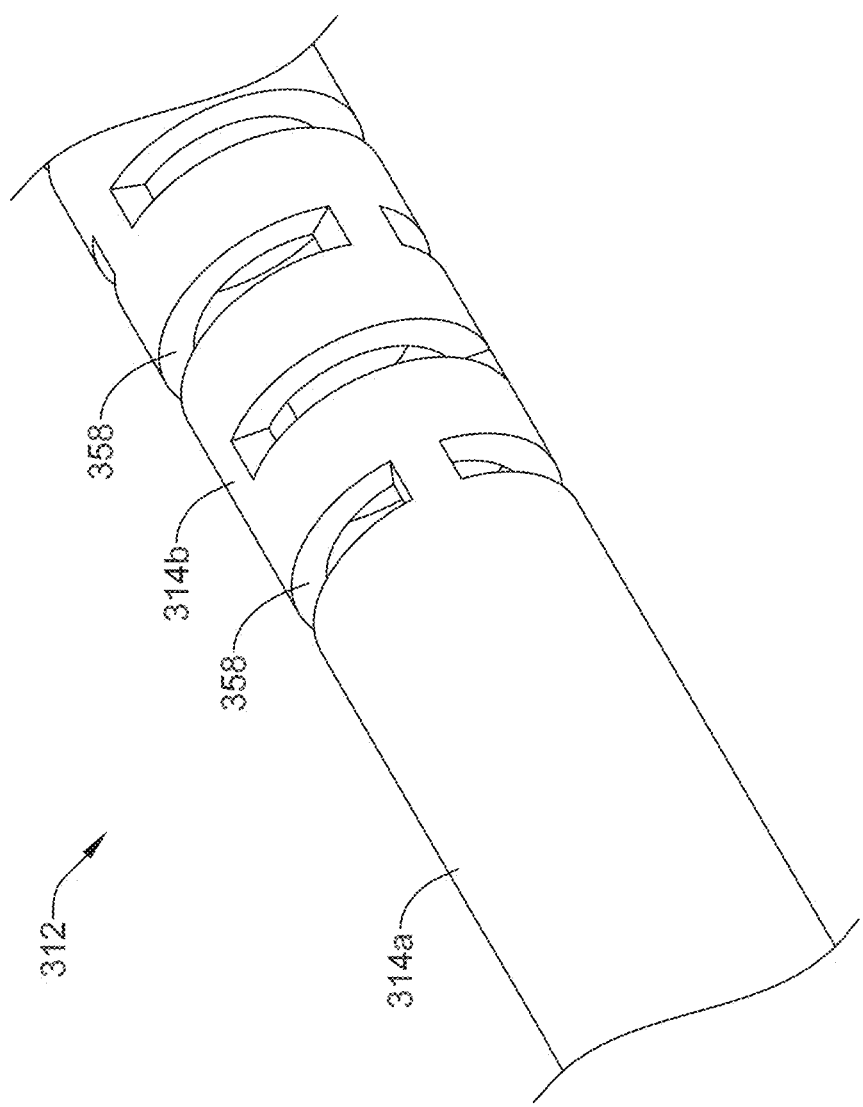
FIG. 12 is a perspective view of another example proximal shaft portion of a catheter shaft.

In addition to being made from a bare metal hypotube having a skew value falling within the range disclosed herein, other variation to the catheter shaft 12 (e.g., proximal shaft portion 14) are also contemplated. For example, FIG. 10 illustrates an example catheter shaft 112 that includes a proximal shaft portion 114 having a spiral cut formed therein. Similarly, FIG. 11 illustrates another example catheter shaft 212 that includes a proximal shaft portion 214 having a plurality of slots 258 formed therein. Moreover, FIG. 12 illustrates another example catheter shaft 312. A first portion 314a of the catheter shaft 312 may be free of slots. A second portion 314b of catheter shaft 312 has a plurality of slots 358 formed therein. Collectively, FIGS. 10-12 illustrate some of the additional variations contemplated for any of the catheter shafts (and/or any of the proximal shaft portions) disclosed herein.

The materials that can be used for the various components of catheter 10 may include those commonly associated with medical devices. For simplicity purposes, the following discussion makes reference to catheter shaft 12 and other components of catheter 10. However, this is not intended to limit the devices and methods described herein, as the discussion may be applied to other similar tubular members and/or components of tubular members or devices disclosed herein.

Catheter shaft 12 and/or other components of catheter 10 may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304 L, and 316 LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Patent Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of catheter shaft 12 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of catheter 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of catheter 10 to achieve the same result.

In some embodiments, a degree of Magnetic Resonance Imaging (MRI) compatibility is imparted into catheter 10. For example, catheter shaft 12, or portions thereof, may be made of a material that does not substantially distort the image and create substantial artifacts (i.e., gaps in the image). Certain ferromagnetic materials, for example, may not be suitable because they may create artifacts in an MRI image. Catheter shaft 12, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

A sheath or covering (not shown) may be disposed over portions or all of catheter shaft 12 that may define a generally smooth outer surface for catheter 10. In other embodiments, however, such a sheath or covering may be absent from a portion of all of catheter 10, such that catheter shaft 12 may form the outer surface. The sheath may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the exterior surface of the catheter 10 (including, for example, the exterior surface of catheter shaft 12) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over portion of catheter shaft 12, or other portions of catheter 10. Alternatively, the sheath may comprise a lubricious, hydrophilic, protective, or other type of coating. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

In addition to variations in materials, various embodiments of arrangements and configurations are also contemplated for the slots (e.g., slots 258/358) disclosed herein. For simplicity purposes, the following discussion makes reference to slots 258 and a tubular member (e.g., a catheter shaft, a portion of a catheter shaft, a bare metal hypotube, etc.). For example, in some embodiments, at least some, if not all of slots 258 are disposed at the same or a similar angle with respect to the longitudinal axis of the tubular member. Slots 258 can be disposed at an angle that is perpendicular, or substantially perpendicular, and/or can be characterized as being disposed in a plane that is normal to the longitudinal axis of the tubular member. However, in other embodiments, slots 258 can be disposed at an angle that is not perpendicular, and/or can be characterized as being disposed in a plane that is not normal to the longitudinal axis of the tubular member. Additionally, a group of one or more slots 258 may be disposed at different angles relative to another group of one or more slots 258. The distribution and/or configuration of slots 258 can also include, to the extent applicable, any of those disclosed in U.S. Pat. Publication No. US 2004/0181174, the entire disclosure of which is herein incorporated by reference.

Slots 258 may be provided to enhance the flexibility of the tubular member while still allowing for suitable torque transmission characteristics. Slots 258 may be formed such that one or more rings and/or tube segments interconnected by one or more segments and/or beams that are formed in the tubular member, and such tube segments and beams may include portions of the tubular member that remain after slots 258 are formed in the body of the tubular member. Such an interconnected structure may act to maintain a relatively high degree of torsional stiffness, while maintaining a desired level of lateral flexibility. In some embodiments, some adjacent slots 258 can be formed such that they include portions that overlap with each other about the circumference of the tubular member. In other embodiments, some adjacent slots 258 can be disposed such that they do not necessarily overlap with each other, but are disposed in a pattern that provides the desired degree of lateral flexibility.

Additionally, slots 258 can be arranged along the length of, or about the circumference of, the tubular member to achieve desired properties. For example, adjacent slots 258, or groups of slots 258, can be arranged in a symmetrical pattern, such as being disposed essentially equally on opposite sides about the circumference of the tubular member, or can be rotated by an angle relative to each other about the axis of the tubular member. Additionally, adjacent slots 258, or groups of slots 258, may be equally spaced along the length of the tubular member, or can be arranged in an increasing or decreasing density pattern, or can be arranged in a non-symmetric or irregular pattern. Other characteristics, such as slot size, slot shape, and/or slot angle with respect to the longitudinal axis of the tubular member, can also be varied along the length of the tubular member in order to vary the flexibility or other properties. In other embodiments, moreover, it is contemplated that the portions of the tubular member, such as a proximal section, or a distal section, or the entire the tubular member, may not include any such slots 258.

As suggested herein, slots 258 may be formed in groups of two, three, four, five, or more slots 258, which may be located at substantially the same location along the axis of the tubular member. Alternatively, a single slot 258 may be disposed at some or all of these locations. Within the groups of slots 258, there may be included slots 258 that are equal in size (i.e., span the same circumferential distance around the tubular member). In some of these as well as other embodiments, at least some slots 258 in a group are unequal in size (i.e., span a different circumferential distance around the tubular member). Longitudinally adjacent groups of slots 258 may have the same or different configurations. For example, some embodiments of the tubular member include slots 258 that are equal in size in a first group and then unequally sized in an adjacent group. It can be appreciated that in groups that have two slots 258 that are equal in size and are symmetrically disposed around the tube circumference, the centroid of the pair of beams (i.e., the portion of the tubular member remaining after slots 258 are formed therein) is coincident with the central axis of the tubular member. Conversely, in groups that have two slots 258 that are unequal in size and whose centroids are directly opposed on the tube circumference, the centroid of the pair of beams can be offset from the central axis of the tubular member. Some embodiments of the tubular member include only slot groups with centroids that are coincident with the central axis of the tubular member, only slot groups with centroids that are offset from the central axis of the tubular member, or slot groups with centroids that are coincident with the central axis of the tubular member in a first group and offset from the central axis of the tubular member in another group. The amount of offset may vary depending on the depth (or length) of slots 258 and can include other suitable distances.

Slots 258 can be formed by methods such as micromachining, saw-cutting (e.g., using a diamond grit embedded semiconductor dicing blade), electrical discharge machining, grinding, milling, casting, molding, chemically etching or treating, or other known methods, and the like. In some such embodiments, the structure of the tubular member is formed by cutting and/or removing portions of the tube to form slots 258. Some example embodiments of appropriate micromachining methods and other cutting methods, and structures for tubular members including slots and medical devices including tubular members are disclosed in U.S. Pat. Publication Nos. 2003/0069522 and 2004/0181174-A2; and U.S. Pat. Nos. 6,766,720; and 6,579,246, the entire disclosures of which are herein incorporated by reference. Some example embodiments of etching processes are described in U.S. Pat. No. 5,106,455, the entire disclosure of which is herein incorporated by reference. It should be noted that the methods for manufacturing catheter 12 may include forming slots 258 in the tubular member using these or other manufacturing steps.

In at least some embodiments, slots 258 may be formed in tubular member using a laser cutting process. The laser cutting process may include a suitable laser and/or laser cutting apparatus. For example, the laser cutting process may utilize a fiber laser. Utilizing processes like laser cutting may be desirable for a number of reasons. For example, laser cutting processes may allow the tubular member to be cut into a number of different cutting patterns in a precisely controlled manner. This may include variations in the slot width, ring width, beam height and/or width, etc. Furthermore, changes to the cutting pattern can be made without the need to replace the cutting instrument (e.g., blade). This may also allow smaller tubes (e.g., having a smaller outer diameter) to be used to form the tubular member without being limited by a minimum cutting blade size. Consequently, tubular members may be fabricated for use in neurological devices or other devices where a relatively small size may be desired.

EXAMPLES

The invention may be further clarified by reference to the following Examples, which serve to exemplify some of the embodiments, and not to limit the invention in any way.

Example 1

A plurality of tubular members were subjected to profilometry and lubricity/friction testing. In the forgoing examples, the hypotubes tested can be identified according to a group designation. The groups were defined as follows:

Group A: hypotubes in this group are 304 L stainless steel hypotubes having an outer diameter of 0.026 inches, an inner diameter of 0.020 inches, and are were obtained from Creganna TACTX Medical (Galway, Ireland). The group A hypotubes were bare metal hypotubes and were free of an outer lubricious coating.

Group B: hypotubes in this group are 304 L stainless steel hypotubes having an outer diameter of 0.025 inches, an inner diameter of 0.019 inches, and are were obtained from Cambus Medical (Galway, Ireland). The group B hypotubes were bare metal hypotubes and were free of an outer lubricious coating.

Group C: hypotubes in this group are 304 stainless steel hypotubes having an outer diameter of 0.025 inches, an inner diameter of 0.019 inches, coated with a 0.0004 inches thick polytetrafluoroethylene (PTFE) coating, and are were obtained from Creganna TACTX Medical (Galway, Ireland).

Group D: hypotubes in this group are 304 L stainless steel hypotubes having an outer diameter of 0.025 inches, an inner diameter of 0.019 inches, coated with a 0.0004 inches thick polytetrafluoroethylene (PTFE) coating, and are were obtained from Cambus Medical (Galway, Ireland).

Group E: hypotubes in this group are 304 L stainless steel hypotubes having an outer diameter of 0.024 inches, an inner diameter of 0.018 inches, and were obtained from Creganna TACTX Medical (Galway, Ireland). The hypotubes in group E were covered with a 0.002 inches thick nylon jacket by Boston Scientific (Maple Grove, Minn.).

Example 2

For the purposes of this disclosure, roughness may be understood to be fine irregularities in the surface of a material or object. Average roughness ($R_a$) may be understood to be the average of the individual heights and depths from the arithmetic mean elevation of the profile of the object.

Skew ($R_{sk}$) is a measure of asymmetry of the profile about the mean line calculated over the evaluation length. Skew may also be understood to be the same as skewness or $R_{sk}$. A negative value of $R_{sk}$ indicates that the surface is made up of valleys, whereas a surface with a positive skew is said to contain mainly peaks. A negatively skewed surface is generally thought to be a lower friction surface.

The surface profilometry was measured in example tubular members. Measurements of the hypotubes were taken using a Veeko Dektak 150 surface profilometry system, with a collet fixture to grasp the hypotube and hold it parallel to the scan axis. The following scan parameters were used on the Dektak 150 system:

2.5 um stylus
Scan length=4064 um
Force=3.00 mg
Profile=Hills and Valleys
Duration=30 sec The raw data generated was exported to EXCEL® software (Microsoft Corporation, Redmond, Wash.). The data was fit to a quadratic equation to account for the stylus moving away from the centerline of the tubular member during testing. The quadratic equation was used to offset the raw data and provide the data with a straight mean line for analysis of $R_a$ and $R_{sk}$.

Figure 13:
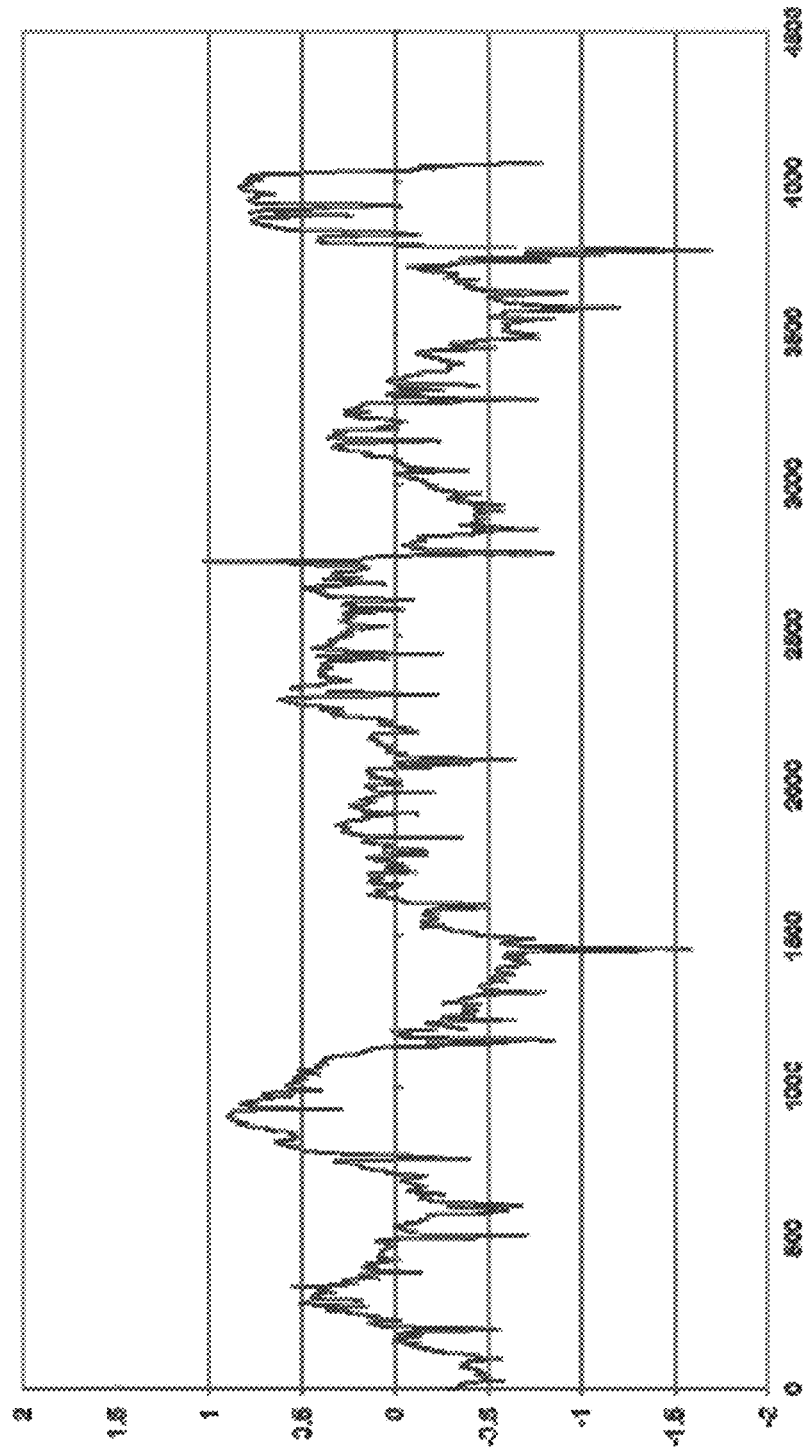
FIGS. 13-14 are graphical representations of profilometry test results for a number of example tubular members.

A graphical depiction of the surface profilometry test results from a representative tubular member from Group A is shown in FIG. 13. The representative tubular member had a skew value of −0.20.

Figure 14:
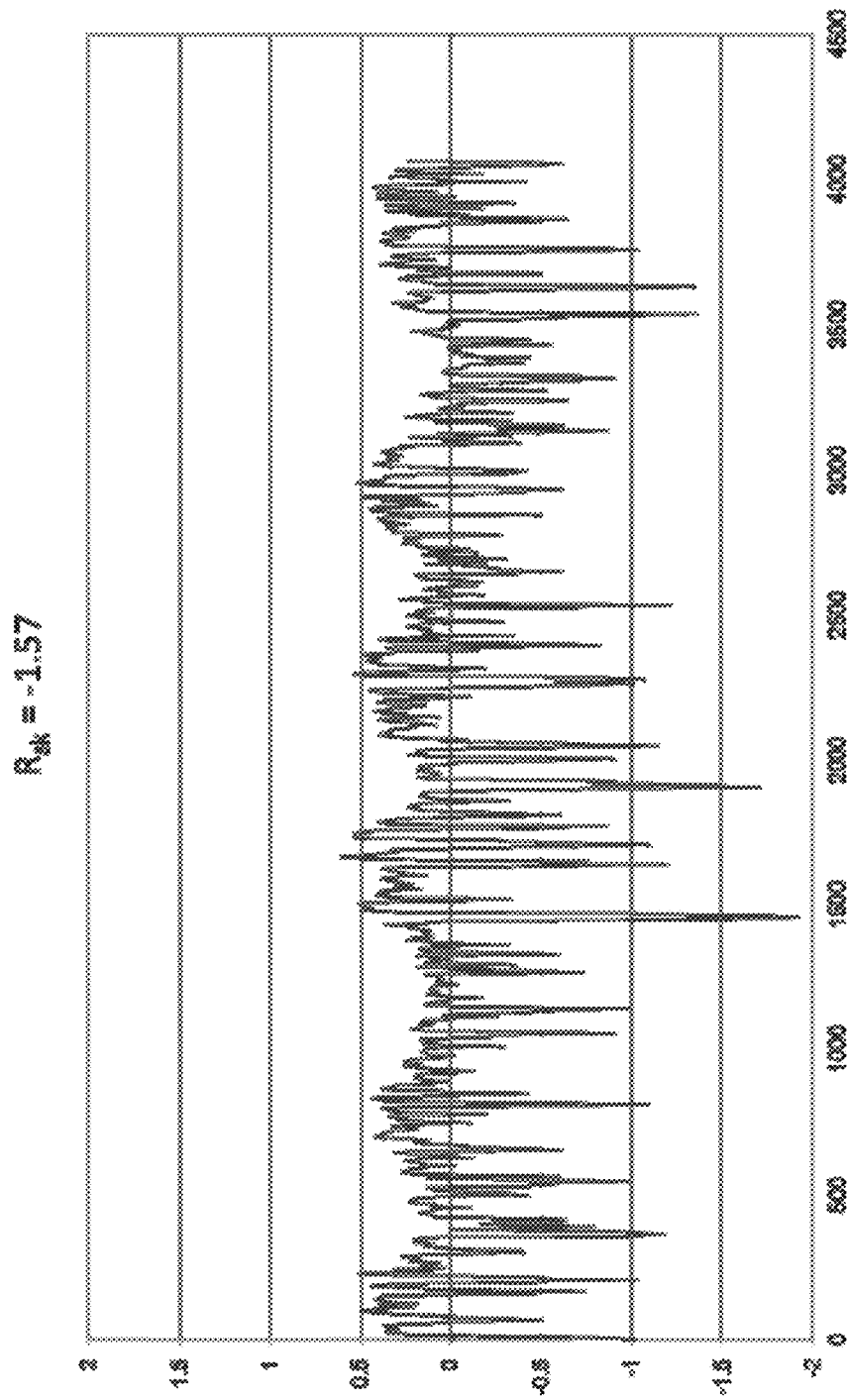

A graphical depiction of the surface profilometry test results from a representative tubular member from Group B is shown in FIG. 14. The representative tubular member had a skew value of −1.57.

A summary of the roughness ($R_a$) and skew values ($R_{sk}$) for 8 sample Group A tubular members is listed in Table 1.

TABLE 1

Roughness ($R_a$) and skew values ($R_{sk}$) for 8 example Group A tubular members

| Tubular Member | $R_a$ (μm) | $R_{sk}$ |
|---|---|---|
| Group A sample 1 | 0.46 | −0.98 |
| Group A sample 2 | Group A sample 1 | Group A sample 1 |
| Group A sample 3 | 0.610 | −0.08 |
| Group A sample 4 | 0.66 | −0.29 |
| Group A sample 5 | 0.67 | −0.63 |
| Group A sample 6 | 0.52 | −0.41 |
| Group A sample 7 | 0.74 | −0.26 |
| Group A sample 8 | 0.66 | 0.06 |

A summary of the roughness ($R_a$) and skew values ($R_{sk}$) for 6 sample Group B tubular members is listed in Table 2.

TABLE 2

Roughness ($R_a$) and skew values ($R_{sk}$) for 6 example Group B tubular members

| Tubular Member | $R_a$ (μm) | $R_{sk}$ |
|---|---|---|
| Group B sample 1 | 0.62 | −1.57 |
| Group B sample 2 | 0.62 | −1.49 |
| Group B sample 3 | 0.62 | −1.42 |
| Group B sample 4 | 0.61 | −1.74 |
| Group B sample 5 | 0.77 | −1.75 |
| Group B sample 6 | 0.80 | −1.79 |

Example 3

A number of example tubular members were tested in an aorto-iliac model test. Briefly, the test involved placing two identical example tubular members (from the appropriate group) within a 6 F guide catheter. The guide catheter was curved. The amount of force required to translate the example tubular members through the guide catheter was measured. The results from the tests are presented in Table 3.

TABLE 3

Summary of aorto-iliac model test results

| Group | Average Force (g) |
|---|---|
| A | 83.7 |
| B | 41.2 |
| C | 54.0 |
| D | 49.6 |
| E | 57.2 |

These results indicated that example tubular members from group B performed better (less frictional resistance) than example tubular members from group A and just as well as (if not better than) example tubular members C, D, and E.

Example 4

A number of example tubular members were tested in catheter with a hemostasis valve. Briefly, the test involved placing two identical example tubular members (from the appropriate group) within a 6 F guide catheter. The guide catheter was straight and had a touhy-borst connector/hemostasis valve at its proximal end. The touhy-borst connector was rotated 1.75 turns to engage the connector with the tubular members (and where the connector exerted a radially-inward force onto the tubular members). The amount of force required to translate the example tubular members through the guide catheter while the connectors was engaged with tubular members was measured. The results from the tests are presented in Table 4.

TABLE 4

Summary of hemostasis valve test results

| Group | Average Force (g) |
|---|---|
| A | 118.8 |
| B | 79.0 |
| C | 90.4 |
| D | 87.6 |
| E | 138.4 |

These results indicated that example tubular members from group B performed better (less frictional resistance) than example tubular members from groups A and E and just as well as (if not better than) example tubular members C and D.

Example 5

A number of example tubular members were tested in a silicone contact surface pinch test. Briefly, the test involved placing an example tubular member (from the appropriate group) between silicon surfaces in an underwater testing apparatus, applying 500g of pinching force on the example tubular members with the silicone surfaces, and measuring the resistance force (e.g., the amount of force required to overcome the friction forces on the example tubular member). The results from the tests are presented in Table 5.

TABLE 5

Silicon contact surface test results

| Group | Average Force (g) |
|---|---|
| A | 111.3 |
| B | 94.3 |
| C | 81.1 |
| D | 95.3 |
| E | 70.8 |

These results indicated that example tubular members from group B performed better (less frictional resistance) than example tubular member A and similar to example tubular members from groups C and D.

The entire disclosures of U.S. Pat. Nos. 6,409,863, 5,156,594, 5,720,724, 6,361,529, and 6,475,187 are herein incorporated by reference.

The entire disclosures of U.S. Patent Application Pub. Nos. US 2010/02172354 and US 2011/0009942 are herein incorporated by reference.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A balloon catheter comprising:
   a proximal shaft including a bare metal hypotube having a negative skew value;
   wherein the bare metal hypotube is free of an outer lubricious coating;
   a midshaft attached to the proximal shaft;
   a distal shaft attached to the midshaft;
   a balloon coupled to the distal shaft; and
   an inflation lumen extending through the proximal shaft, the midshaft, and into the distal shaft, the inflation lumen being in fluid communication with the balloon.
2. The balloon catheter of claim 1, wherein the skew value of the bare metal hypotube is −1.0 to −2.0.
3. The balloon catheter of claim 1, wherein the skew value of the bare metal hypotube is −1.0 to −1.75.
4. The balloon catheter of claim 1, wherein the skew value of the bare metal hypotube is −1.25 to −1.8.
5. The balloon catheter of claim 1, wherein the skew value of the bare metal hypotube is −1.4 to −1.8.
6. The balloon catheter of claim 1, wherein the skew value of the bare metal hypotube is −1.42 to −1.79.
7. The balloon catheter of claim 1, wherein the skew value of the bare metal hypotube is −1.47 to −1.75.
8. The balloon catheter of claim 1, wherein the skew value of the bare metal hypotube is −1.57 to -1.74.
9. The balloon catheter of claim 1, wherein the bare metal hypotube includes stainless steel.
10. The balloon catheter of claim 1, wherein the bare metal hypotube has a plurality of slots formed therein.
11. A catheter, comprising:
    a catheter shaft ;
    wherein at least a portion of the catheter shaft includes a bare metal hypotube that is free of an outer lubricious coating, the bare metal hypotube having a negative skew value.
12. The catheter of claim 11, wherein the bare metal hypotube has a skew value of −1.0 to −2.0.
13. The catheter of claim 11, wherein the catheter shaft is a balloon catheter shaft.
14. The catheter of claim 11, wherein the catheter shaft is a guide catheter shaft.
15. The catheter of claim 11, wherein the catheter shaft is a stent delivery catheter shaft.
16. The catheter of claim 11, wherein the bare metal hypotube includes stainless steel.
17. The catheter of claim 11, wherein the bare metal hypotube has a plurality of slots formed therein.
18. A balloon catheter comprising:
    a proximal shaft including a bare metal hypotube having an outer surface and a plurality of valleys formed within the outer surface to reduce a frictional value of the outer surface;
    wherein the bare metal hypotube is free of an outer lubricious coating;
    a midshaft attached to the proximal shaft;
    a distal shaft attached to the midshaft;
    a balloon coupled to the distal shaft; and
    an inflation lumen extending through the proximal shaft, the midshaft, and into the distal shaft, the inflation lumen being in fluid communication with the balloon.
19. The balloon catheter of claim 18, wherein the bare metal hypotube has a negative skew value that is between -2.5 and -1.0.

* * * * *